(12) United States Patent
Menassa

(10) Patent No.: US 7,357,781 B2
(45) Date of Patent: Apr. 15, 2008

(54) NEEDLELESS INJECTOR

(76) Inventor: Karim Menassa, 2773 Carre Denise Pelletier, Montreal, Quebec (CA) H4R 2T3

( * ) Notice: Subject to any disclaimer, the term of this patent is extended or adjusted under 35 U.S.C. 154(b) by 369 days.

(21) Appl. No.: 10/503,915

(22) PCT Filed: Jan. 22, 2003

(86) PCT No.: PCT/CA03/00068

§ 371 (c)(1),
(2), (4) Date: Aug. 9, 2004

(87) PCT Pub. No.: WO03/068296

PCT Pub. Date: Aug. 21, 2003

(65) Prior Publication Data

US 2005/0085767 A1 Apr. 21, 2005

(30) Foreign Application Priority Data

Feb. 12, 2002 (CA) .................................. 2371466

(51) Int. Cl.
*A61M 5/30* (2006.01)

(52) U.S. Cl. ........................................................ 604/70
(58) Field of Classification Search ............ 604/68–72
See application file for complete search history.

(56) References Cited

U.S. PATENT DOCUMENTS

| 4,342,310 A | * | 8/1982 | Lindmayer et al. ............ 604/70 |
| 5,569,190 A | * | 10/1996 | D'Antonio .................... 604/72 |
| 6,004,287 A | * | 12/1999 | Loomis et al. ................ 604/68 |
| 6,440,105 B1 | * | 8/2002 | Menne ........................ 604/218 |

* cited by examiner

*Primary Examiner*—Kevin C. Sirmons
*Assistant Examiner*—Catherine N. Witczak
(74) *Attorney, Agent, or Firm*—George A. Seaby

(57) ABSTRACT

A needleless injector includes a barrel for receiving an injectable liquid, a nozzle closing one end of the barrel containing an injection orifice, and a plunger and piston combination in the barrel. A valve admits gas under pressure into the barrel behind the piston. A trigger opens the valve to cause the piston to move against the plunger, and a magnet retains the piston in a rest position in the barrel until acted upon by the gas under sufficient pressure to cause the piston and plunger to move to an extended, discharge position.

12 Claims, 19 Drawing Sheets

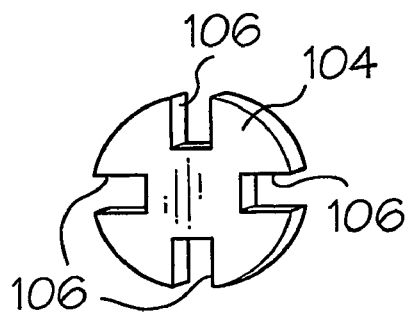 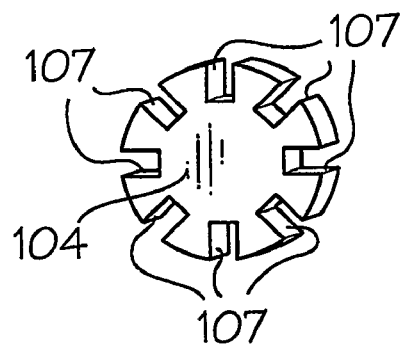
FIG. 11  FIG. 12
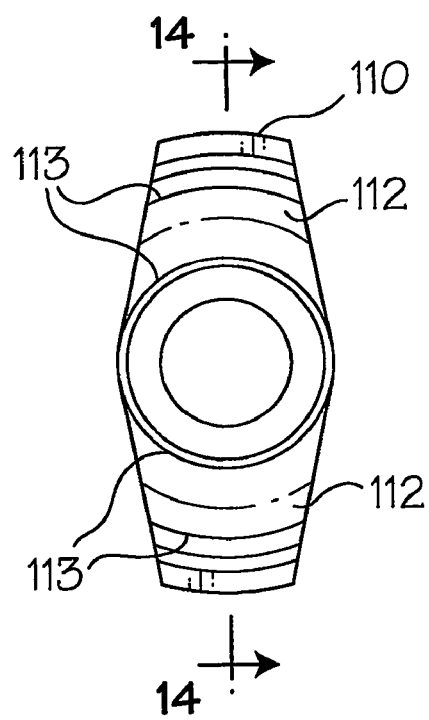 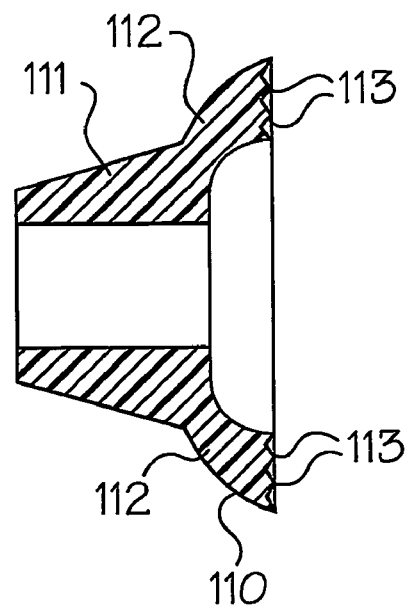
FIG. 13  FIG. 14

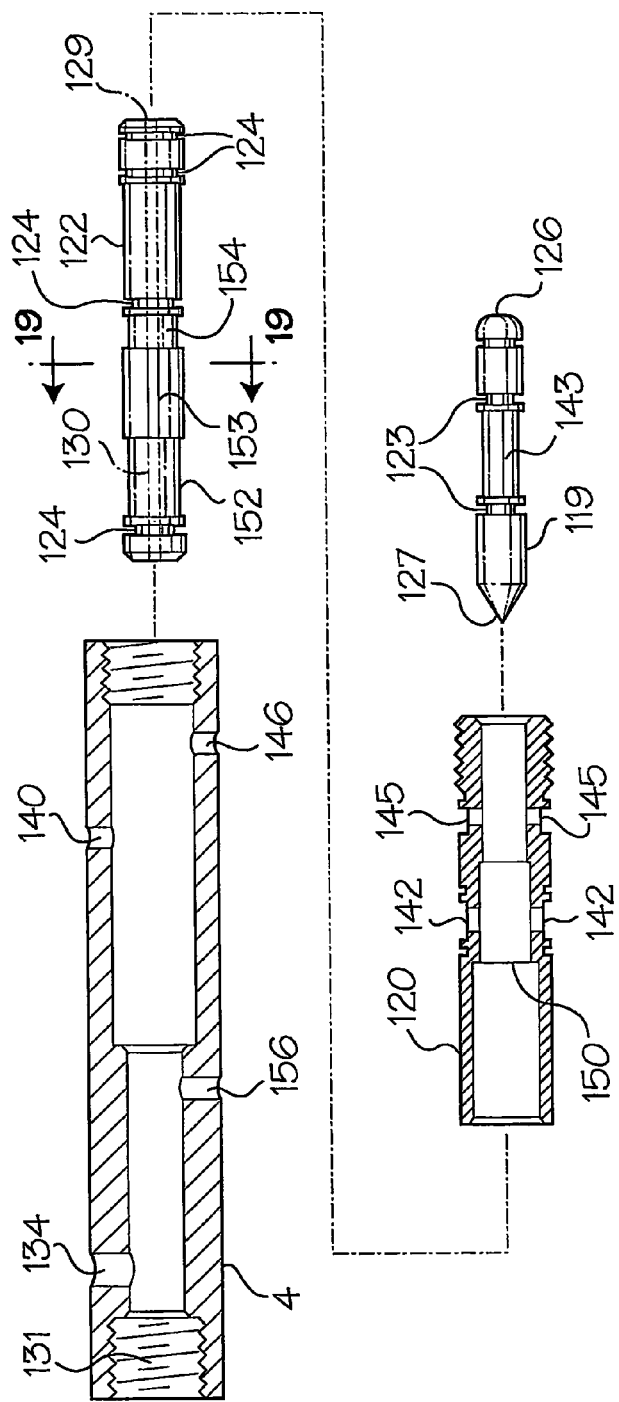
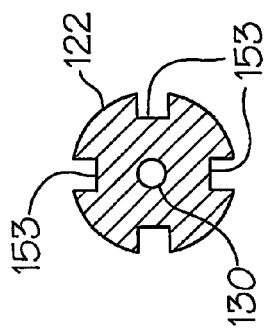
FIG. 18
FIG. 19

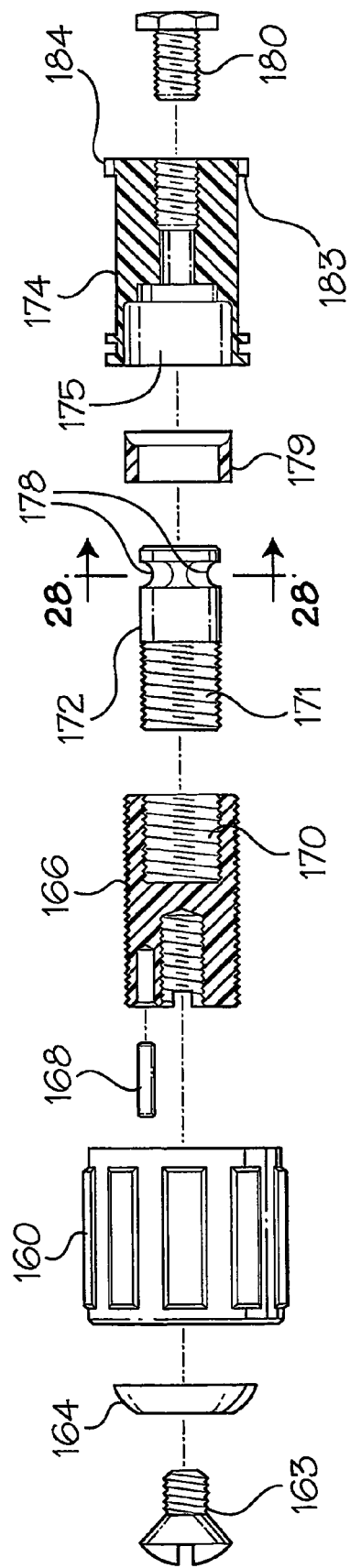
FIG. 26
FIG. 28
FIG. 27

NEEDLELESS INJECTOR

This invention relates to an injector and in particular to a needleless injector.

As described in U.S. Pat. No. 5,507,911, issued to J. S. Parsons on Jan. 6, 1998, needleless or jet injectors administer medicine without using needles. The use of jet injectors results in less pain and reduces environmental contamination due to needle disposal. There is a surprisingly large number of patents relating to small, gas or spring operated, tubular injectors which must be reloaded after each injection. Such single use injectors are impractical when injecting a medicine into a large number of persons or animals, e.g. when carrying out mass vaccinations.

Multi-use injectors are disclosed, for example by U.S. Pat. No. 2,928,390, issued to A. Venditty et al on Mar. 15, 1960; U.S. Pat. No. 3,054,349, issued to A. Ismach on Oct. 9, 1962; U.S. Pat. No. 3,526,225, issued to M. Isobe on Sep. 1, 1970; U.S. Pat. No. 3,805,783, issued to A. Ismach on Sep. 29, 1972; U.S. Pat. No. 3,859,996, issued to A. R. Mizzy et al on Jan. 14, 1975 and U.S. Pat. No. 4,342,310, issued to 1. Lindmayer et al on Aug. 3, 1982. As stated in the Parsons patent, few jet injectors have achieved commercial success. In fact, precious few injectors of this type have ever been commercialized to any large extent.

One problem with existing devices is the ability to control the dosage; i.e. the provision of means for easily adjusting the dosage, which may vary from person to person or animal to animal. When using an injector for injecting horses, cows, pigs and chickens, it must be possible to change the dosage depending upon the animal being treated. Otherwise, it is necessary to provide separate injectors for each type of animal. Another problem with existing injectors is that of re-cocking the devices following injections. When carrying out a large number of injections, it must be possible to almost instantaneously re-load and re-cock the injector in preparation for successive injections.

An object of the present invention is to provide solutions to the above-mentioned problems in the form of a relatively simple needleless injector, which can be used to carry out a plurality of successive injections quickly.

Another object of the invention is to provide a mechanism for quickly and easily adjusting the dosage of the injector.

Accordingly, the invention relates to a needleless injector comprising:

barrel means for receiving an injectable liquid from a source thereof;

nozzle means in one end of said barrel means for discharging liquid from said barrel means;

plunger means slidable in said barrel means for movement between a retracted position in which liquid is drawn into said barrel means between said nozzle means and said plunger means and an extended position in which liquid is discharged through said nozzle means;

piston means slidable in said barrel means for retaining said plunger means in the retracted position and movable under fluid pressure to move said plunger means to the extended position;

first valve means for introducing fluid under pressure into said barrel means on either side of said piston means, whereby the piston means and plunger means can be moved between the retracted and extended positions;

trigger means for operating said first valve means to cause said plunger means to move from the retracted to the extended position and then back to the retracted position each time the trigger means is operated stop means in a second end of said barrel means remote from said one end for limiting movement of the piston means when the plunger means and piston means move to the retracted position; and magnet means in said piston means releasably retaining the piston means and plunger means in the retracted position until the trigger is operated.

The invention is described below in greater detail with reference to the accompanying drawings, which illustrate a preferred embodiment of the invention, and wherein:

FIGS. 11 and 12 are isometric views of spacers used in the nozzle end of the injector on a large scale;

FIG. 13 is a front view of a stretcher used on the nozzle end of the injector;

FIG. 14 is a cross section taken generally along line 14-14 of FIG. 13;

FIG. 18 is an exploded view of a lower cylinder and valve used in the injector of FIGS. 1 and 2;

FIG. 19 is cross section taken generally along line 19-19 of FIG. 18;

FIG. 26 is a partly sectioned, exploded side view of the stroke adjusting mechanism of FIG. 25;

FIG. 27 is an end view of the adjusting mechanism of FIG. 25 as seen from the right thereof;

FIG. 28 is a cross section taken generally along line 28-28 of FIG. 26;

Figure 1:
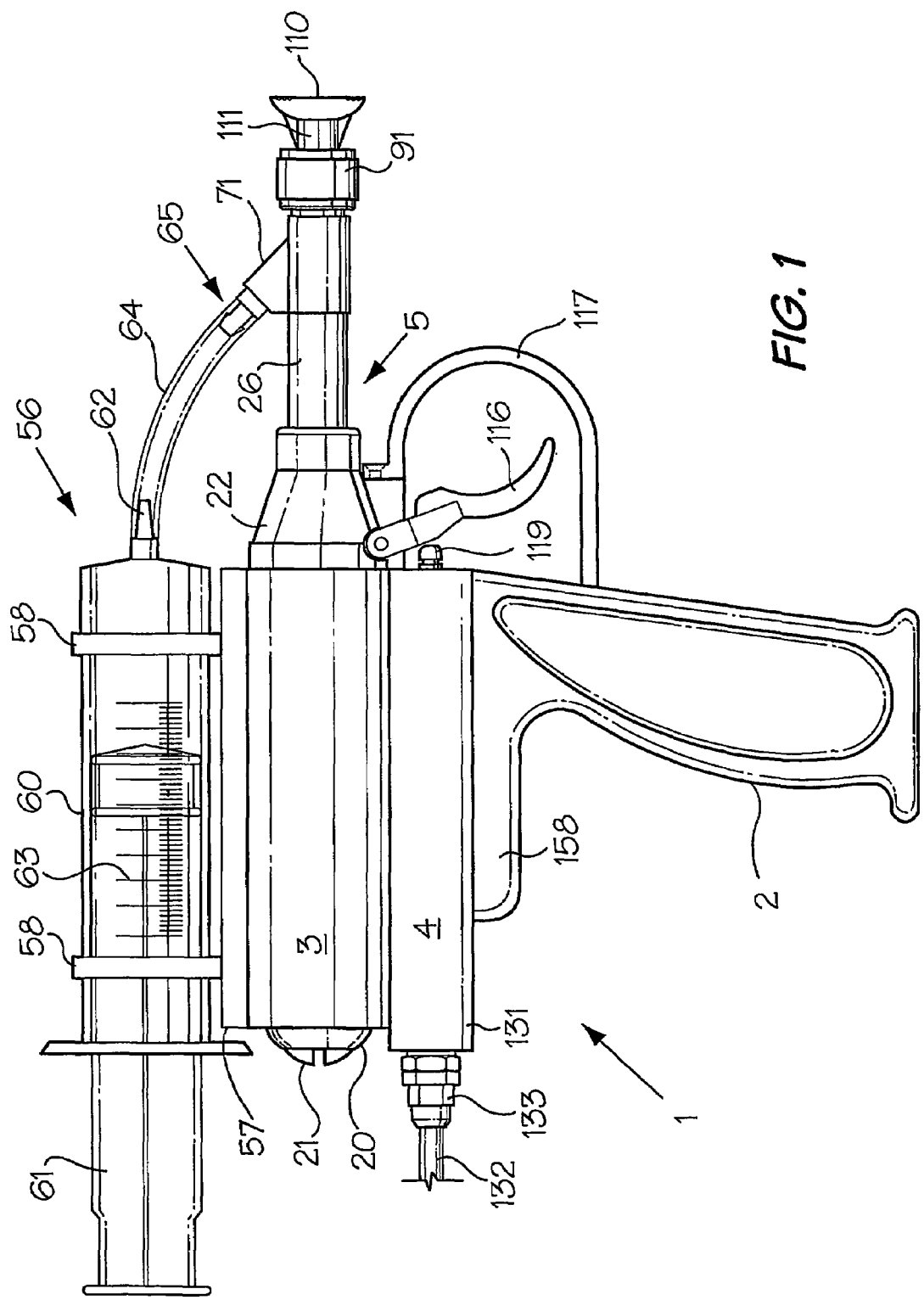
FIG. 1 is a side view of a needleless injector in accordance with the invention.

It should be noted that in the following detailed description of preferred embodiments of the invention the same reference numerals have been used in various views of the drawings to identify the same or similar elements. Moreover, for the sake of simplicity, parts have been omitted from some figures of the drawings.

Figure 2:
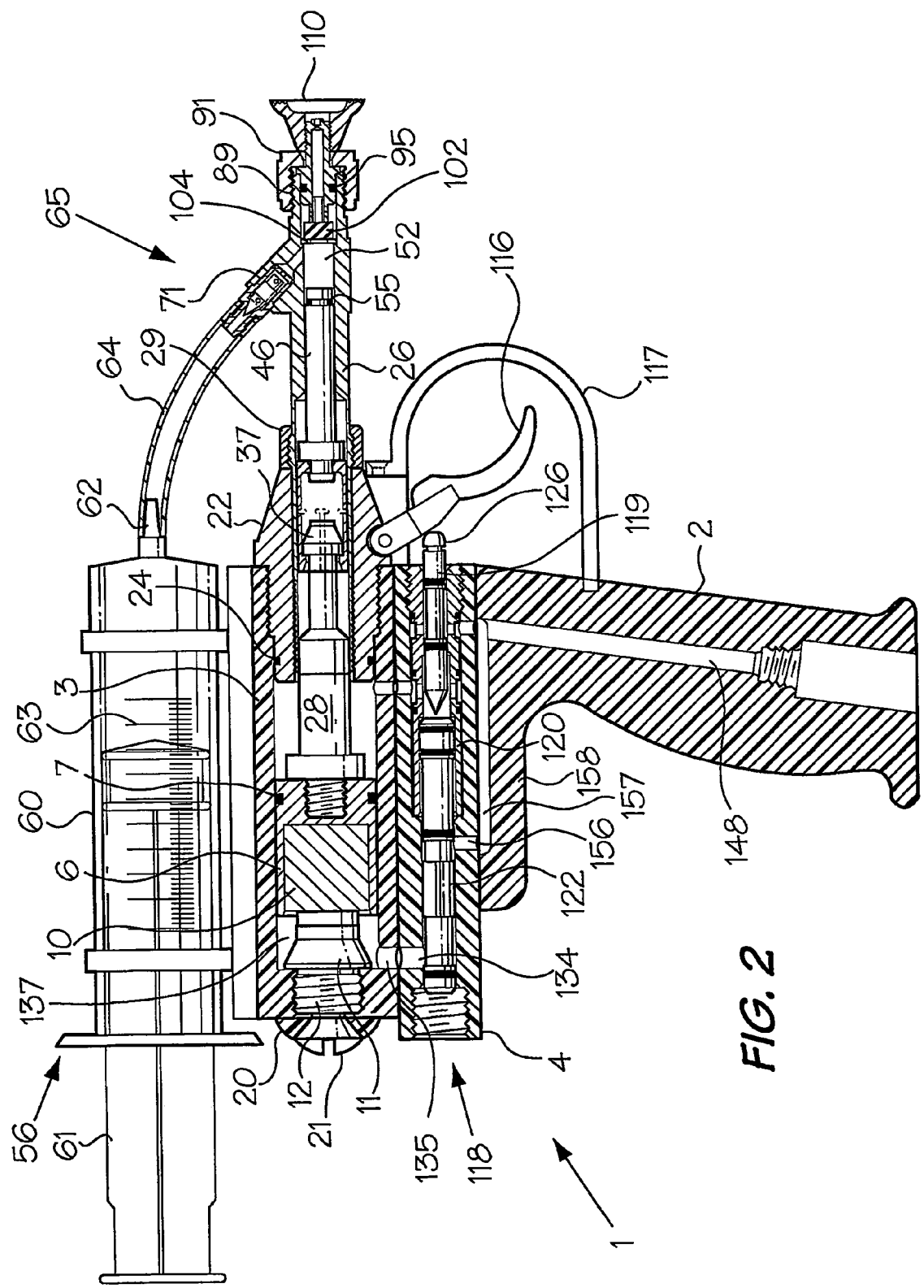
FIG. 2 is a longitudinal sectional view of the injector of FIG. 1.

Referring to FIGS. 1 and 2, the injector of the present invention is in the shape of a pistol, and includes a body indicated generally at 1 with a handle 2 extending outwardly from approximately the center thereof. The body 1 is defined by upper and lower cylinders 3 and 4, respectively which contain most of the remaining elements of the injector. The cylinder 3 defines one end of a barrel indicated generally at 5 (FIG. 1).

A brass piston 6 is slidably mounted in the cylinder 3. An O-ring 7 seals the piston 6 in the cylinder 3. The piston 6 is generally cup-shaped, including a rear recess 8 (FIG. 3) for receiving a cylindrical, permanent magnet 10. The piston 6 and the magnet 10 are retained in the cylinder 3 by a plug 11 formed of ABS (acrylonitrile-butadiene-styrene) plastic which has a threaded outer end 12 for engaging internal threads 14 (FIG. 3) on an inwardly extending annular flange 15 on the rear end of the cylinder 3. A shoulder 17 on the plug 11 limits outward movement of the plug 11 in the cylinder 3. A head 18 with a threaded stem 19 is mounted on the inner end of the plug 11 for bearing against the rear end of the magnet 10. An ABS plastic washer 20 is held on the rear end of the cylinder 3 by a screw 21. By removing the screw 21, a screw driver (not shown) can be inserted into the notched rear end of the plug 11 and rotated to change the position of the plug in the cylinder. By changing the position of the plug 11 in the cylinder, the stroke of the piston 6 is adjusted. Thus, the plug 11 acts as a stop for the piston 6 and as part of a stroke adjusting mechanism for the injector.

The externally threaded rear end of an ABS plastic sleeve 22 is mounted in the internally threaded front end of the cylinder 3. An O-ring 24 seals the sleeve 22 in the cylinder 3. The threaded end 25 of an elongated tube 26 is mounted in the cap 22 for receiving the leading end of a retractor 28. It will be appreciated that the sleeve 22 and the tube 26 complete the elongated barrel 5, which slidably supports the piston 6, the retractor 28 and other elements of the injector, as described below in greater detail. The tube 26 is centered in the cap 22 by a cylindrical nut 29, which engages threads 30 on the barrel near the middle thereof. The threaded rear end 32 (FIG. 3) of the retractor 28 is screwed into a threaded recess 33 in the front end of the piston 6. A ring 34 on the retractor 28 limits movement of the retractor into the piston 6 and acts as a bearing surface for the piston.

Figure 3:
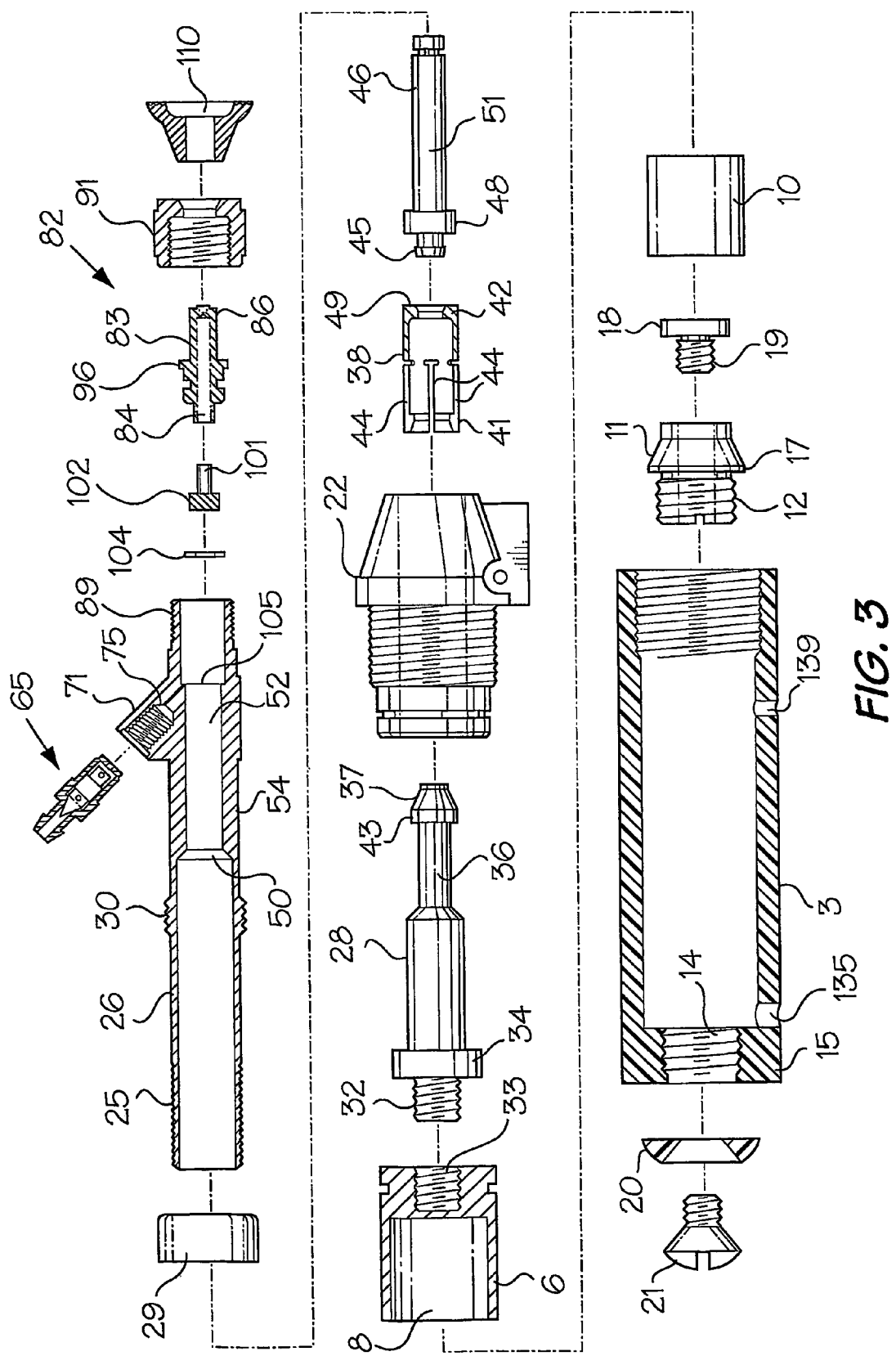
FIG. 3 is an exploded view of the top portion of the injector of FIGS. 1 and 2 with parts omitted.
Figure 4:
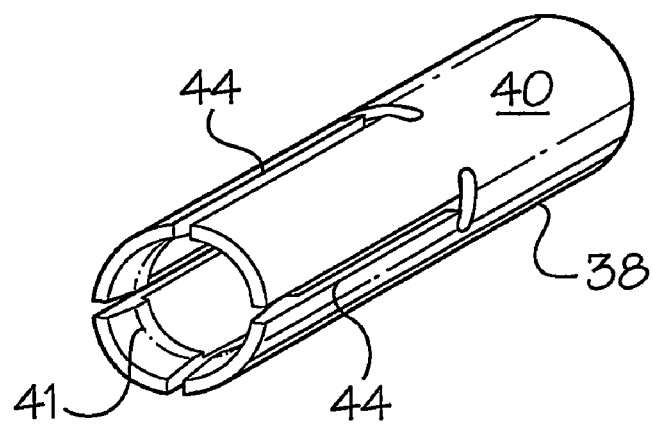
FIG. 4 is an isometric view of a coupler used in the injector of FIGS. 1 and 2 on a large scale.

The front end 36 of the retractor 28 has a reduced diameter. A tapered head 37 on the retractor 28 is slidably mounted in a coupler 38. As best shown in FIGS. 3 and 4, the coupler 38 includes a tubular body 40 with radially inwardly extending flanges 41 and 42 at its rear and front ends, respectively. A shoulder 43 behind the head 37 of the retractor 28 engages the rear flange 41 during rearward movement of the retractor 28 to move the coupler 38 rearwardly. Longitudinally extending, generally T-shaped slots 44 in the body 40 of the coupler 38 permit flexing of the rear end of the body 40 and insertion of the head 37 of the retractor 28 into the coupler during assembly.

A small head 45 on the rear end of a plunger 46 is retained in the coupler 38 by the flange 42, and an annular flange 48 a short distance from the head 45 of the plunger 46 acts as a bearing surface for the front end 49 of the coupler 38 during rearward movement thereof. The flange 48 also limits forward movement of the plunger 46 in the barrel 26 by engaging a shoulder 50 in the barrel at the end of a forward stroke of the plunger. The main body 51 of the plunger 46 slides in a chamber 52 (FIG. 2) in the reduced diameter front end 54 of the barrel 26. The plunger 46 is sealed in the barrel 26 by an O-ring 55. Rearward movement of the plunger 46 in the barrel 26 creates a partial vacuum in the chamber 52 to draw medicine into the chamber from a syringe generally indicated at 56. A bracket defined by a base 57 and loops 58 hold the syringe 56 on the cylinder 3. The syringe 56 is a conventional plastic syringe including a barrel 60 with a plunger 61 slidable in one end thereof for discharging liquid through a narrow diameter nozzle 62 at the other end thereof. The syringe barrel includes a scale 63 indicative of the dosage injected each time the injector is operated. It will be appreciated that the syringe 56 can be replaced by a medicine bottle or bag.

Figure 5:
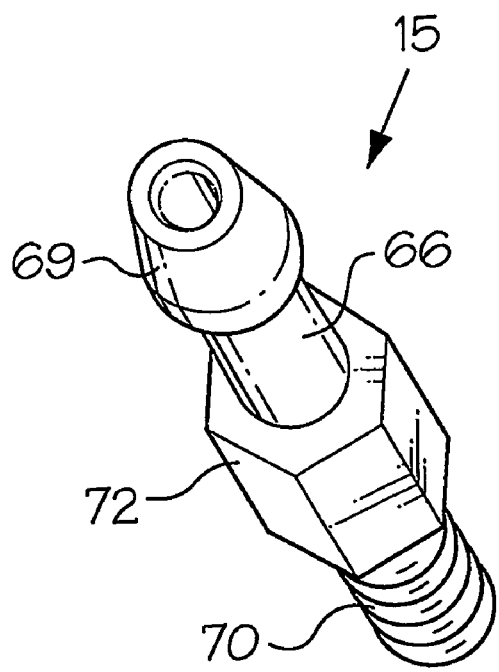
FIG. 5 is an isometric view of a valve used in the injector of FIGS. 1 and 2 on a large scale.
Figure 6:
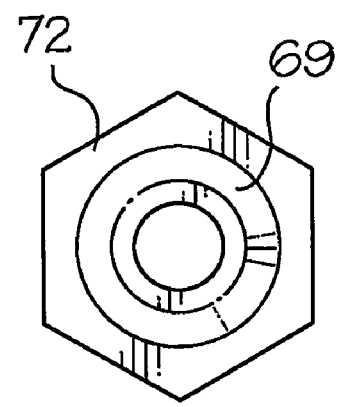
FIG. 6 is a top end view of the valve of FIG. 5.

The liquid discharged from the nozzle 62 passes through a plastic tube 64 and a one-way valve indicated generally at 65 into the chamber 52. As best shown in FIGS. 5 and 6, the valve 65 includes a tubular body 66 and a valve piston or stem 68 slidable therein. A tapered end 69 of the valve body 66 is inserted into the tube 64, and the other, threaded end 70 of the body is mounted in an internally threaded, inclined inlet 71 integral with the barrel. The middle 72 of the valve body 66 is hexagonal in cross section for facilitating mounting in the inlet 71 using a wrench. Movement of the stem 68 is limited by a valve seat 73 defined by a shoulder in the body 66, and the tapered bottom end of a passage 75 (FIGS. 3 and 10) through the inlet 71.

Figure 7:
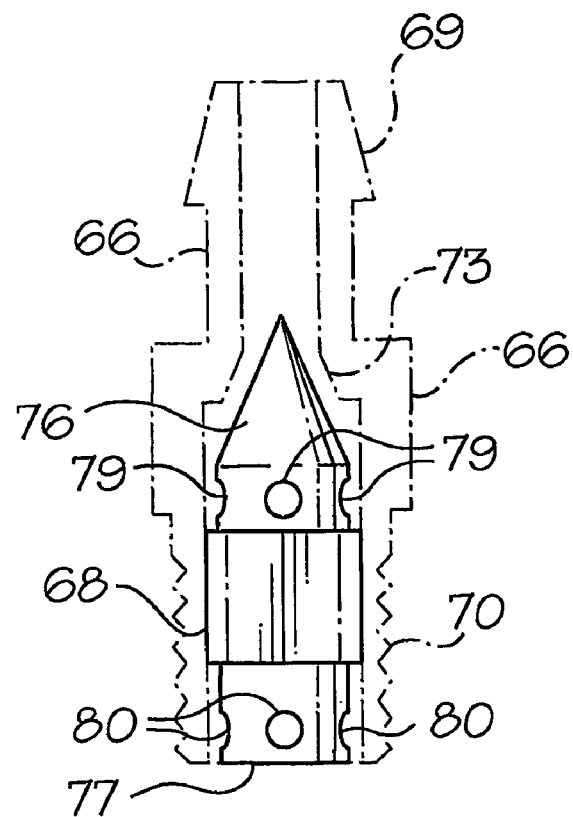
FIG. 7 is a side view of a stem used in the valve of FIGS. 5 and 6.
Figure 8:
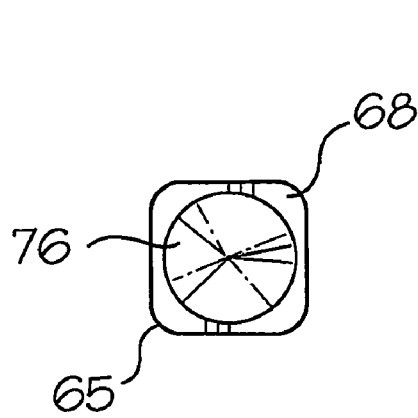
FIG. 8 is a top view of the stem of FIG. 7.
Figure 9:
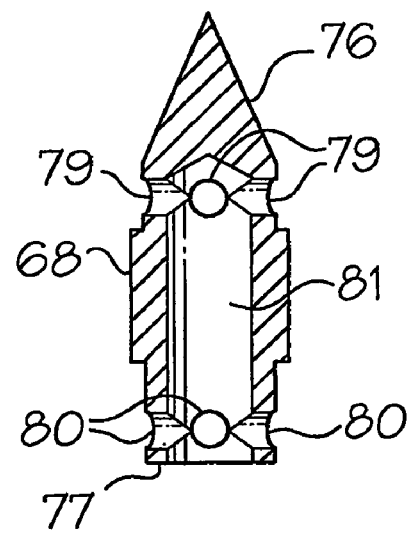
FIG. 9 is a longitudinal sectional view of the stem of FIGS. 7 and 8.

Referring to FIGS. 7 and 9, the valve stem 68 has a generally square cross section, with cylindrical top and bottom ends, 76 and 77, respectively. The top end 76 tapers to a point. Radially extending openings 79 and 80 immediately below the top end 76 and immediately above the bottom end 77 of the stem 68 permit the flow of liquid entering the top end of the valve body 66 into and out of a central passage 81 in the stem. When the chamber 52 is under partial vacuum, i.e. when being discharged therefrom via a nozzle indicated generally at 82 in the front end of the barrel 26.

The nozzle 82 is defined by a tubular body 83 with a passage 84 therethrough. Liquid is discharged from the outlet end 86 of the body 83 via a ruby crystal (not shown) containing a small diameter orifice. The ruby crystal is mounted in a socket 87 in the outlet end 86 in front of a small opening 88. The body 83 is retained in the externally threaded outlet end 89 of the barrel 26 by an internally threaded cap 91 mounted on the externally threaded end 89 of the barrel 26.

Figure 10:
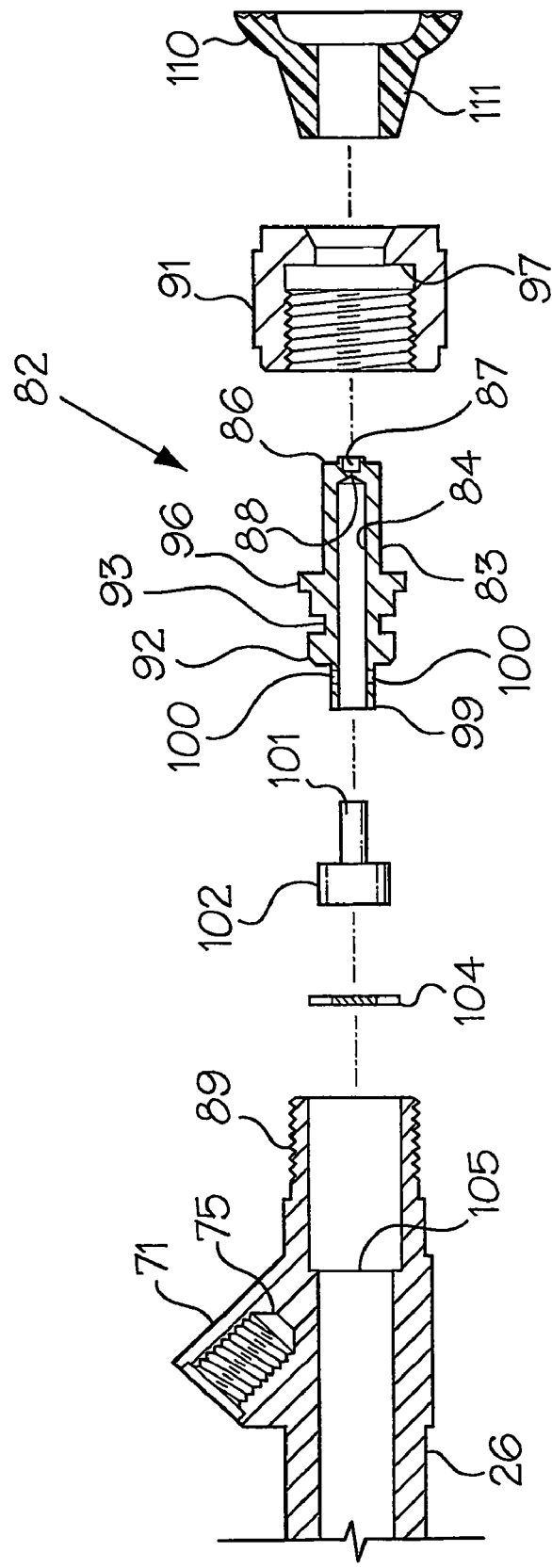
FIG. 10 is an exploded, longitudinal sectional view of one end of a barrel and a nozzle used in the injector of FIGS. 1 and 2.

Referring to FIG. 10, the nozzle body 83 includes a large diameter rear section 92 containing an annular groove 93 for receiving an O-ring 95 (FIG. 2). An annular flange 96 on the middle of the body 83 is sandwiched between the outlet end 89 of the barrel 26 and an inwardly extending, annular flange 97 on the outlet end of the cap 91. The narrow diameter inlet end 99 of the nozzle body 83, which contains diametrically aligned openings 100, receives a hollow valve stem 101 extending outwardly from one side of a disc-shaped, flexible rubber valve head 102. A circular, stainless steel spacer 104 is sandwiched between the valve head 102 and a shoulder 105 in the barrel 26. The head 102 has a smaller diameter than that of the spacer 104. As shown in FIG. 11, the spacer 104 includes four diametrically opposed, rectangular notches 106 or a plurality of notches 107 (FIG. 12) in the periphery thereof. The notches 106 or 107 permit the flow of liquid around the valve head 102. When the liquid in the barrel is subjected to a sufficiently high pressure, liquid flows through the notches 106 and 107, and through the openings 100 compressing the valve stem 101, whereby liquid is discharged under pressure through the nozzle 82.

Figure 17:
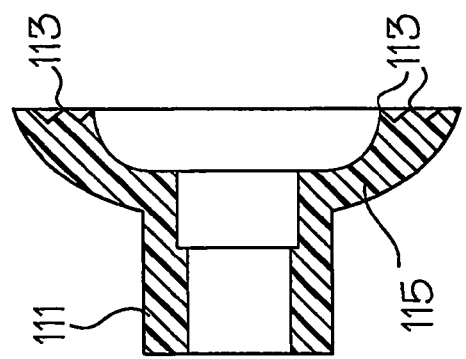
FIG. 17 is a cross section taken generally along line 17-17 of FIG. 16.
Figure 16:
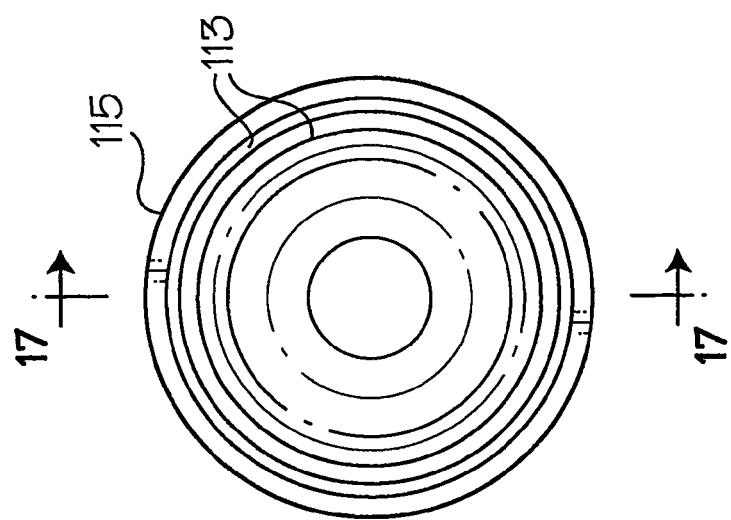
FIG. 16 is a front view of an alternative form of stretcher.
Figure 15:
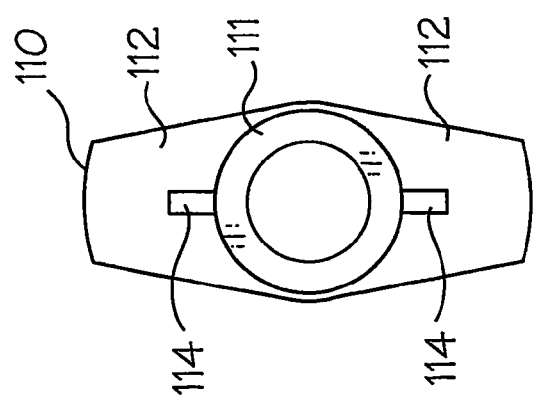
FIG. 15 is a rear view of the stretcher of FIGS. 13 and 14.

A rubber spreader 110 is mounted on the outlet or discharge end of the nozzle body 83, i.e. on the end of the nozzle body 83 outside of the cap 91. The spreader 110 includes a sleeve 111 (FIGS. 1 and 14) for friction mounting on the outlet end 86 of the nozzle body 83. A pair of arcuate arms 112 extend outwardly from the sleeve 111. Sawtooth projections 113 on the arms 112 are intended to grip the skin when the spreader is pressed thereagainst to provide a smooth area for injection. Reinforcing gussets 114 (FIG. 15) extend between the sleeve 111 and the arms 112. The spreader of FIGS. 16 and 17 is similar to that of FIGS. 13 to 15, except that the body 115 of the spreader is circular with annular sawtooth projections 113.

Referring again to FIG. 2, injection is effected using compressed gas from a source (not shown) thereof when a trigger 116 is squeezed. The trigger 116 is pivotally mounted on the bottom of the sleeve 22 inside of a trigger guard 117. The guard 117 extends between the sleeve 22 in front of the trigger 116 and the front of the handle 2. Squeezing of the trigger 116 opens a valve indicated generally at 118. The valve 118 includes a plunger 119 slidably mounted in a sleeve 120 (FIG. 18) in the lower cylinder 4 and a stem 122. The plunger 119 is sealed in the sleeve 120 by O-rings in grooves 123, and the stem 122 is sealed in the rear end of the sleeve 120 and in the lower cylinder 4 by O-rings in annular grooves 124 (FIG. 18). The hemispherical front end 126 of the plunger 119 extends out of the handle 2 into engagement with the trigger 116. The conical inner end 127 of the plunger 119 extends into a socket 129 defined by the front end of a central passage 130 extending longitudinally through the valve stem 122.

Figure 20:
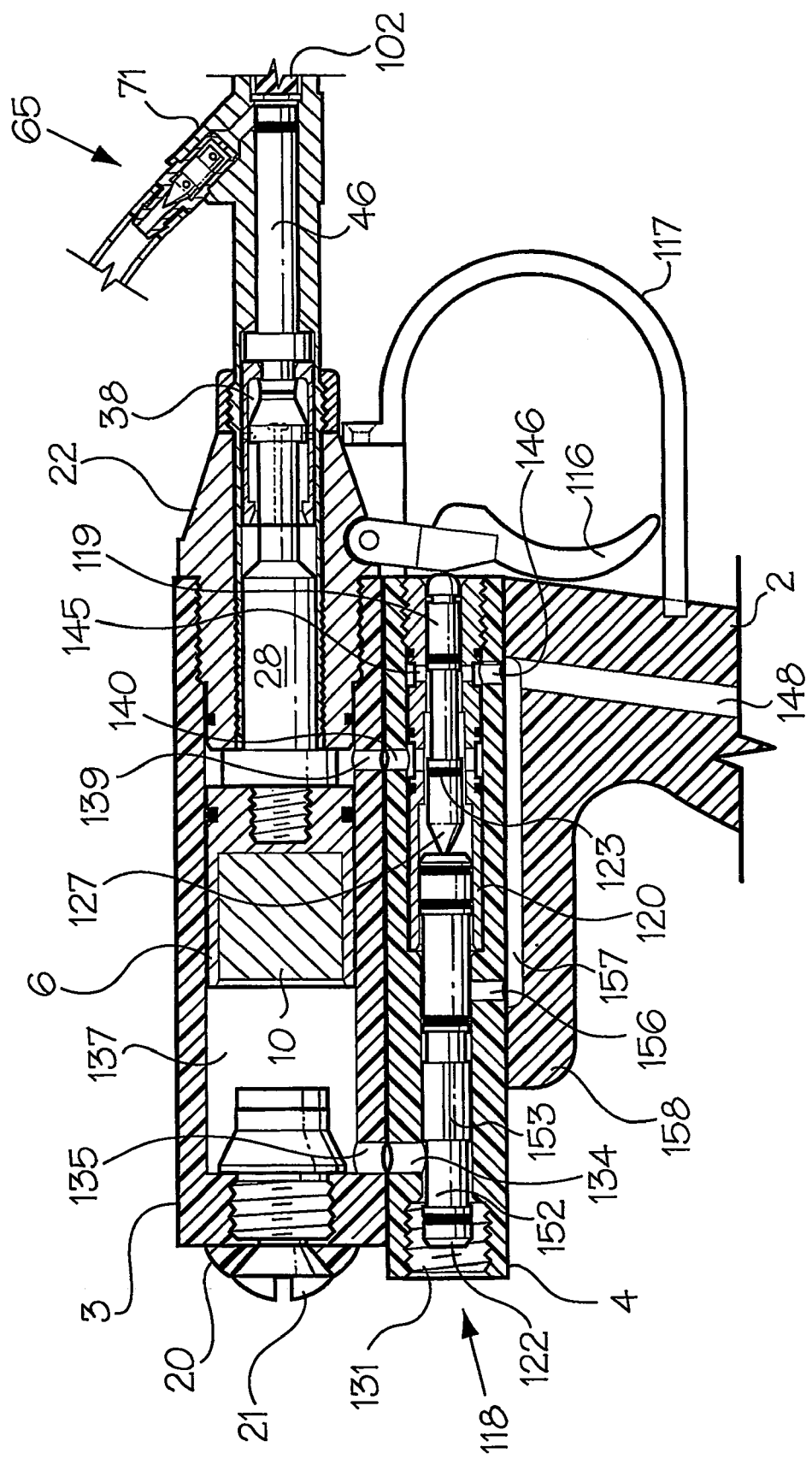
FIG. 20 is a longitudinal sectional view of a portion of the injector of FIG. 1 following an injection.

Assuming that there is liquid from the syringe 56 in the chamber 52, when the trigger 116 is squeezed, the plunger 119 moves rearwardly, pushing the stem 122 rearwardly which permits compressed air to enter the rear, internally threaded, inlet end 131 of the cylinder 4. Such inlet end 131 is connected to a source of gas under pressure, e.g. a compressor by a hose 132 and a connector 133. The air flows through aligned openings 134 and 135 in the lower cylinder 4 and in the upper cylinder 3, respectively into the area 137 behind the piston 6. The compressed air overcomes the force of the magnet 10 driving the piston 6 and consequently the retractor 28 and the plunger 46 forwardly to discharge the liquid from the chamber 52 via the valve and nozzle 82. Any air in the upper cylinder 2 between the piston 6 and the sleeve 22 is forced out through openings 139 and 140 in the cylinders 3 and 4, respectively, and diametrically aligned openings 142 (FIG. 18) in the sleeve 120. As shown in FIG. 20, when the plunger 119 moves with the valve stem 122 to the open position (to the left in FIG. 20), one end of a reduced diameter central portion 143 of the plunger 119 becomes aligned with the openings 139, 140 and 142, and the other end of the reduced diameter portion 143 becomes aligned with openings 145 in the other end of the sleeve 122, with an opening 146 in the bottom cylinder 4 and with a vertical passage 148 in the handle 2 for venting air from in front of the piston 6 to the atmosphere. After the liquid has been discharged from the chamber 52, i.e. when the plunger 46 reaches its forwardmost position against the spacer 105, air entering the cylinder 4 and flowing through the central passage 130 of the valve stem 122 returns the valve stem, the plunger 119 and the trigger 116 to the rest or cocked positions (FIG. 2). When the valve stem 122 reaches the rest position against a shoulder 150 (FIG. 18) in the sleeve 120, air is discharged through the open front end of the passage 130 in the valve stem 122. It will be noted that the plunger 119 has been pushed by the compressed air to a position spaced apart from the front end of the valve stem 122. The air passes through the aligned openings 140 and 139 (FIG. 21) in the cylinders 4 and 3, respectively into the area between the front end of the piston 6 and the rear end of the sleeve 22. At the same time air in the chamber 137 behind the piston 6 is discharged via the opening 135 in the upper cylinder 3, the opening 134 in the lower cylinder 4, a passage between a reduced diameter portion 152 of the valve stem 122 and the cylinder 4, longitudinally extending grooves 153 in the stem 122, a passage between a second reduced diameter portion 154 of the stem, an outlet opening 156 in the lower cylinder 4, a horizontal passage 157 between a top arm 158 of the handle 3 and the lower cylinder 4, and the vertical passage 148. The passage 157 is defined by a groove in the top of the arm 158 of the handle 2 which intersects the passage 148. Since its moving elements have returned to the rest or start position, the injector is ready to be fired again.

With reference to FIGS. 21 to 28, a second embodiment of the injector is similar in most respects to the apparatus of FIGS. 1 to 20, and accordingly (as mentioned above) the same reference numerals are used to identify the same or similar elements.

The second embodiment of the injector includes a different mechanism for adjusting the stroke of the piston 6. For the most part, the mechanism is housed in the chamber 137 behind the piston 6. The mechanism includes a cup-shaped knob 160 rotatably mounted on the rear end of the cylinder 3 for longitudinal movement to adjust the stroke of the piston 6 and consequently the quantity of fluid forced from the injector, i.e. the dosage. A scale 161 (FIGS. 22 and 23) on the side of the cylinder 3 provides an indication of the dosage setting of the knob 160. As mentioned hereinbefore the scale on the syringe barrel 60 also provides an indication of dosage. A screw 163 extends through a washer 164 and the closed end 165 (FIG. 21) of the knob 160 into a threaded shaft 166. A pin 168 extending through the end 165 of the knob 160 into the shaft 166 causes rotation of the knob and the shaft as a unit. The threads on the shaft 166 mate with the internally threaded, open rear end of the cylinder 3.

Figure 21:
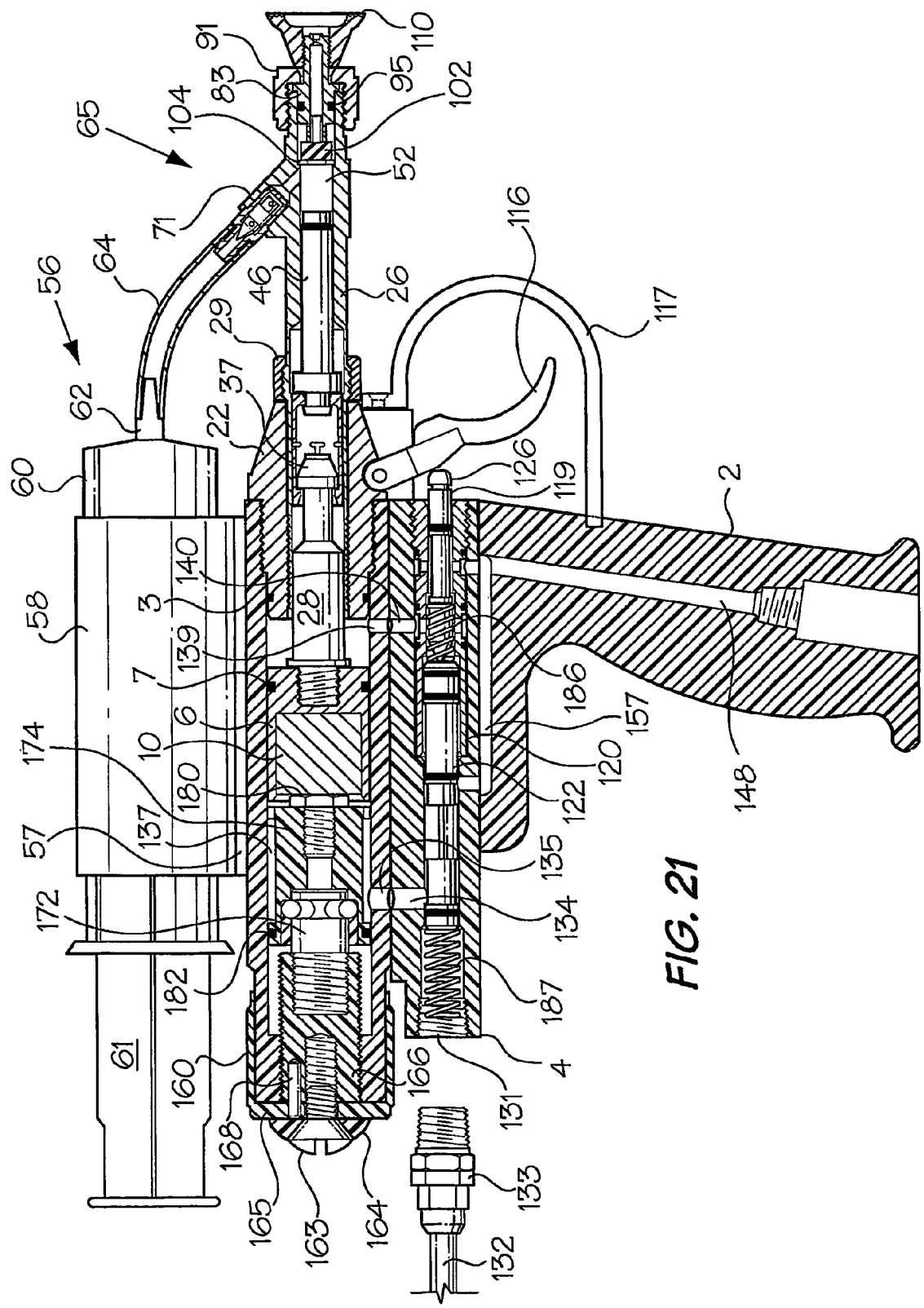
FIG. 21 is a longitudinal sectional view of a second embodiment of the needleless injector.
Figure 22:
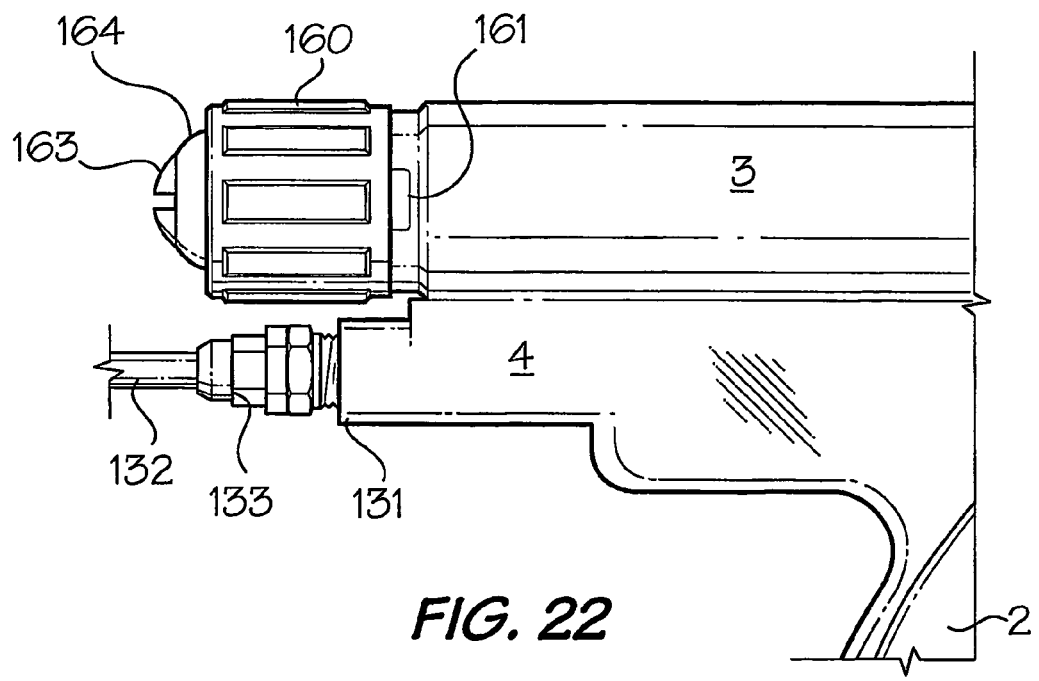
FIGS. 22 and 23 are side views of one end of the injector of FIG. 21.
Figure 23:
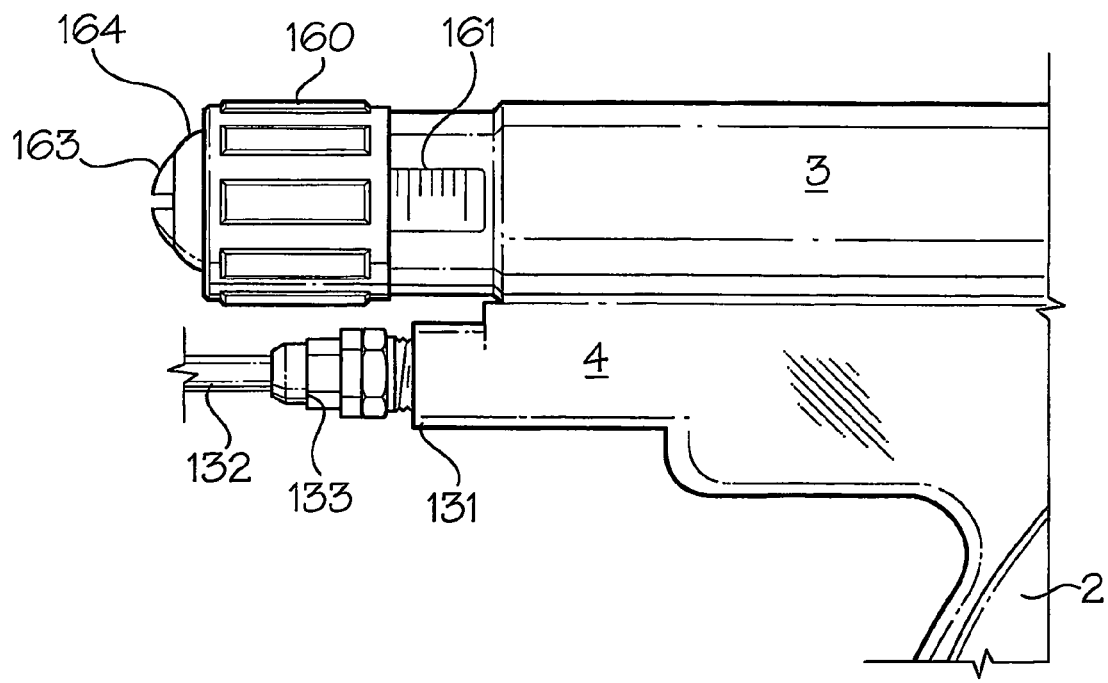
Figure 24:
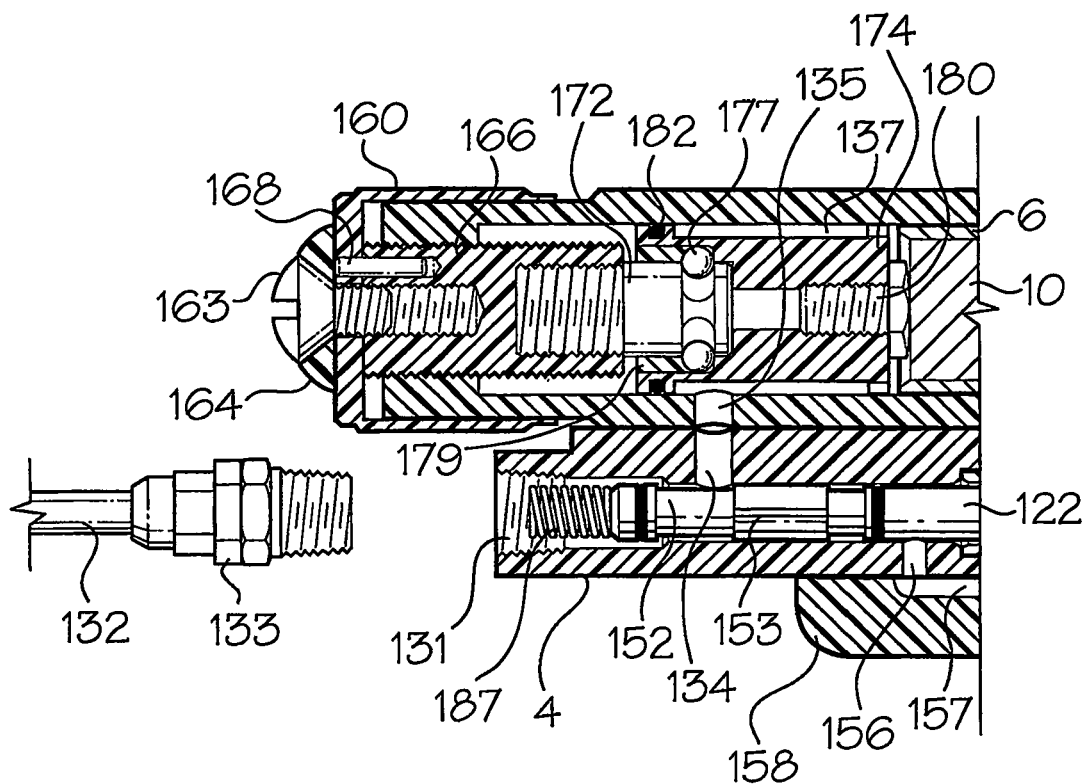
FIG. 24 is a partly exploded, longitudinal sectional view of the end of the injector shown in FIGS. 22 and 23.
Figure 25:
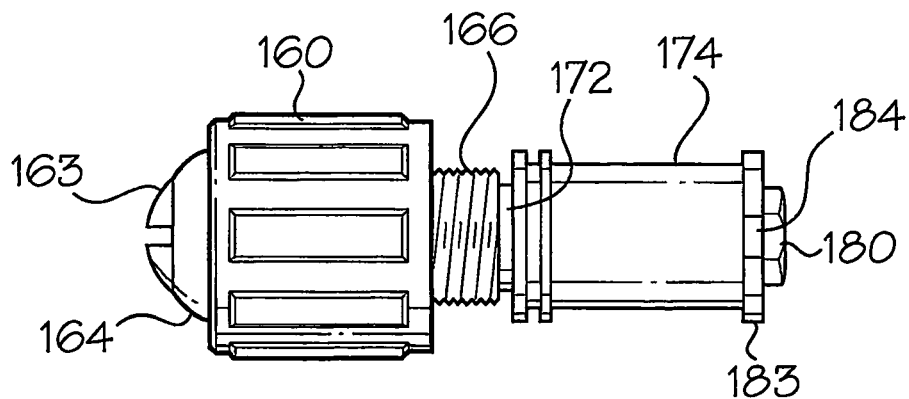
FIG. 25 is a side view of a stroke adjustment mechanism used in the injector of FIG. 21.

The inner end of the shaft 166 contains a threaded bore 170 for retaining the threaded end 171 of a cylindrical connector 172, which connects the shaft 166 to a slide 174 slidably mounted in the cylinder 3 between the shaft 166 and the piston 6. As best shown in FIG. 26, a cylindrical well 175 is provided in the rear or outer end of the slide 174 for receiving the inner end of the connector 172. Ball bearings 177 (FIG. 24) in the concave recesses 178 in the connector 172 permit rotation of the connector in the slide 174 when the shaft 166 is rotated, i.e. rotation of the shaft 166 results in longitudinal movement but not rotation of the slide 174 in the cylinder 3. The ball bearings 177 and the connector 172 are retained in position in the slide 174 by a washer 179. A bolt 180 in the inner end of the slide body engages the magnet 10 to retain the piston 6 in retracted position until acted upon by gas under pressure. The rear end of the slide 174 is sealed in the chamber by an O-ring 182 (FIGS. 21 and 24). An annular flange 183 with rectangular notches 184 therein permits the flow of gas entering the chamber to the rear end of the piston 6 and the magnet 10 to force the piston forwardly towards the plunger 46.

In another embodiment of the invention, the ball bearings 177 and the washer 179 can be omitted, and the shaft 166, the connector 172 and the slide 174 can be combined as a single threaded shaft rotatably mounted in the end of the barrel 3 for rotation by the knob 160. The threaded shaft moves longitudinally of the barrel 3 when rotated to adjust the stroke of the piston 6 and thus the dosage. The adjusting mechanism of FIGS. 21 to 28 and the variation described immediately above permit much larger dosage adjustments than the mechanism of FIG. 2.

Another feature of the injector of FIG. 21 is the use of a pair of helical springs 186 and 187 on the plunger 119 and the valve stem 122, respectively. The springs 186 and 187 speed the return of the trigger 116, the plunger 119 and the valve stem 122 to the rest position (FIG. 21).

Figure 29:
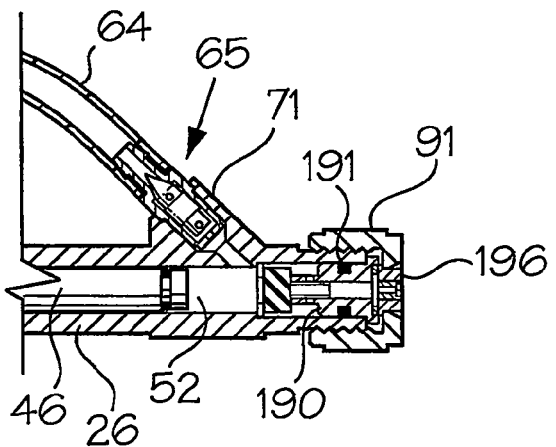
FIG. 29 is a longitudinal sectional view of an alternative form of discharge end for the injector of FIG. 1 or 21.
Figure 30:
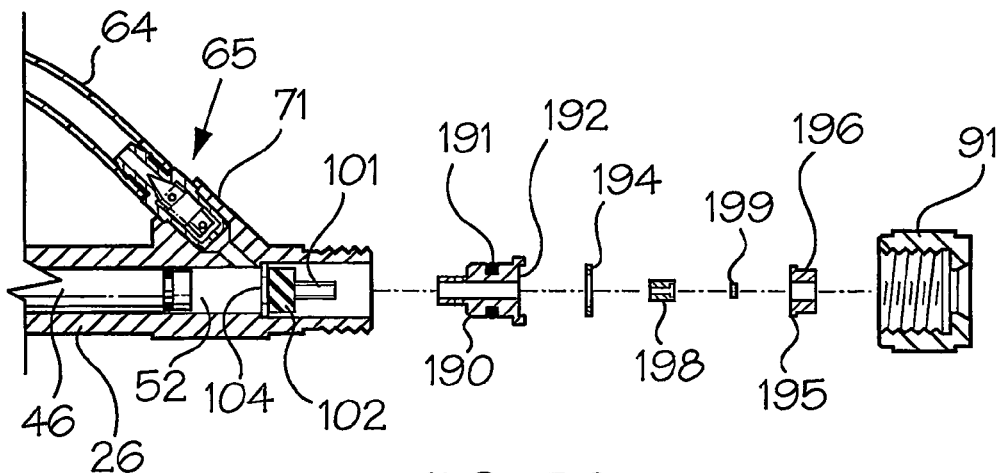
FIG. 30 is an exploded, longitudinal sectional view of the discharge end of the injector shown in FIG. 29.

Referring to FIGS. 29 and 30, the nozzle used in the injector can include a two-part body, rather than the one-piece body as in the injector of FIGS. 1 and 21 for facilitating replacement of a single injection orifice nozzle with multiple orifice nozzles. The nozzle of FIGS. 29 and 30 includes a rear portion 190 for receiving the stem 101 of the valve at the inlet end of the nozzle. The rear portion 190 is sealed in the outlet end of the barrel 26 by an O-ring 191. A circular recess 192 (FIG. 30) in the front or outer end of the rear portion 190 receives a washer 194.

Figure 31:
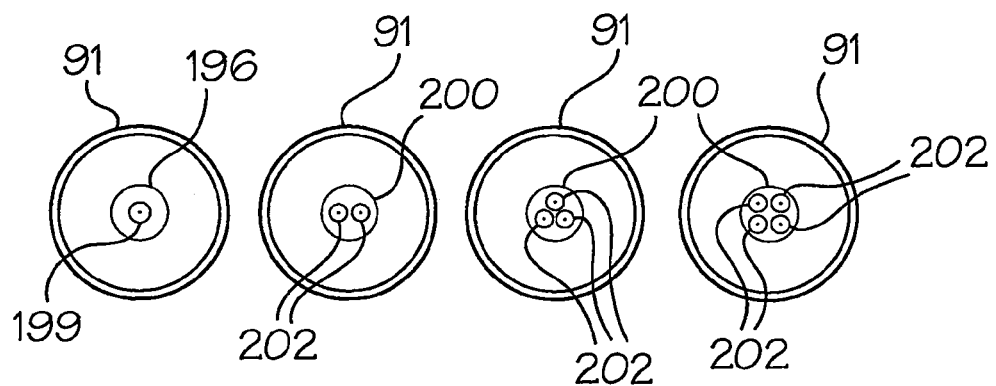
FIG. 31 is a plurality of front end views of single and multiple discharge orifice injectors.
Figure 32:
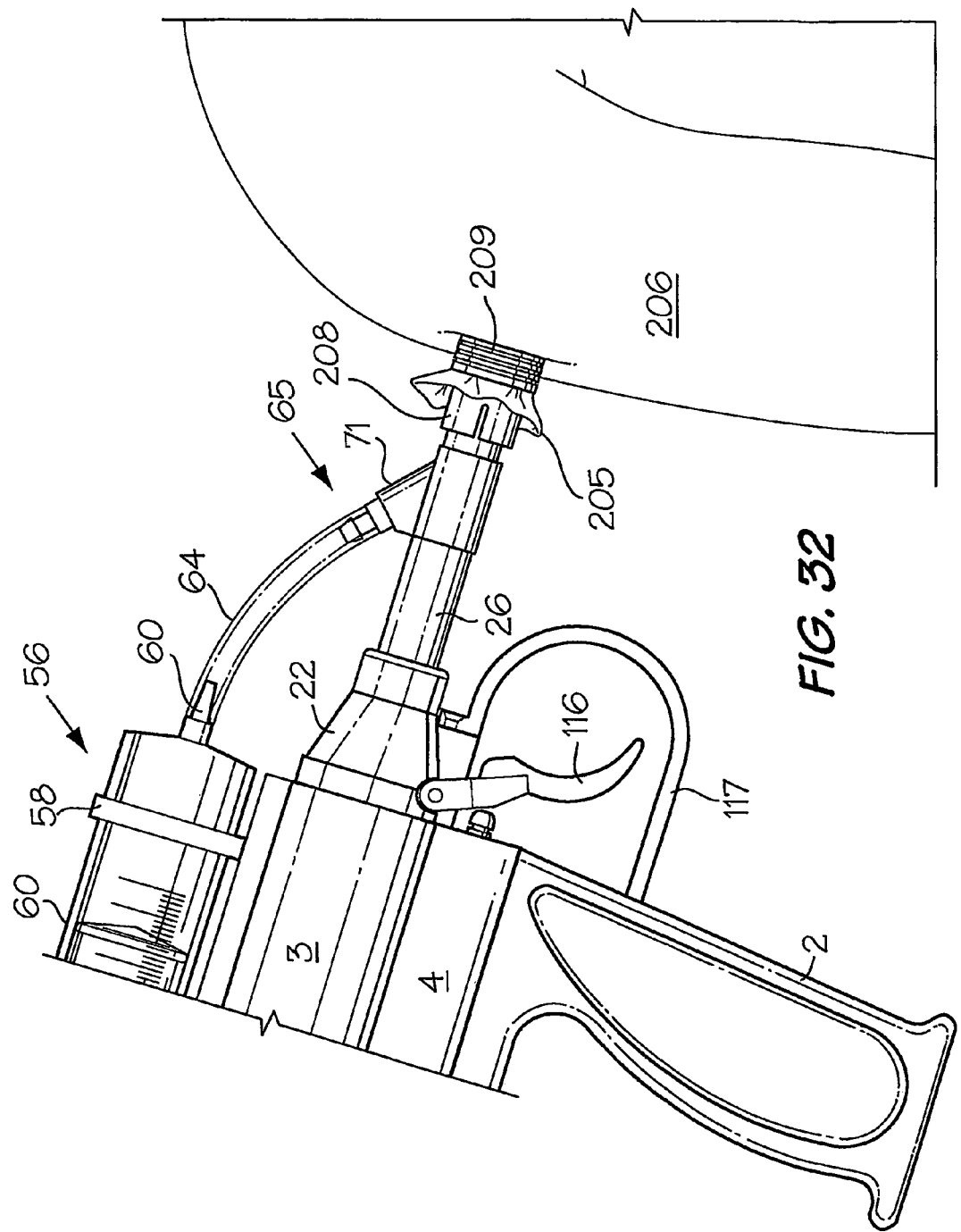
FIG. 32 is a side view of the discharge end of the injector during injection through a sterile pad.

A flange 195 on the front portion 196 of the nozzle presses against the washer 194 when the nozzle is assembled. The front portion 196 of the nozzle is held in position by the cap 91, which engages the flange 195. A sleeve 198 inserted into the rear end of the front nozzle portion 196 carries a ruby crystal 199 (FIG. 30) containing a single injection orifice. It is a relatively simple matter to remove the cap 91, and replace the single orifice front portion 196 of the nozzle with other front portions 200 (FIG. 31) containing two, three or four passages and ruby crystals 202, each containing a single orifice. Multiple orifice nozzles are used when injecting under high pressure, so that medicine is injected into fat underlying the skin, rather than into muscle.

With reference to FIGS. 32 to 39, for extra protection, sterile injection can be effected by the novel method of injecting through a sterile pad 205. The use of a sterile pad 205 obviates the need for alcohol or another disinfectant, and eliminates the possibility of cross contamination. Although a pad 205 can merely be held manually between the skin of a person 206 and the nozzle of the injector, it is preferable to mount the pad in a holder on the end of the injector.

Figure 33:
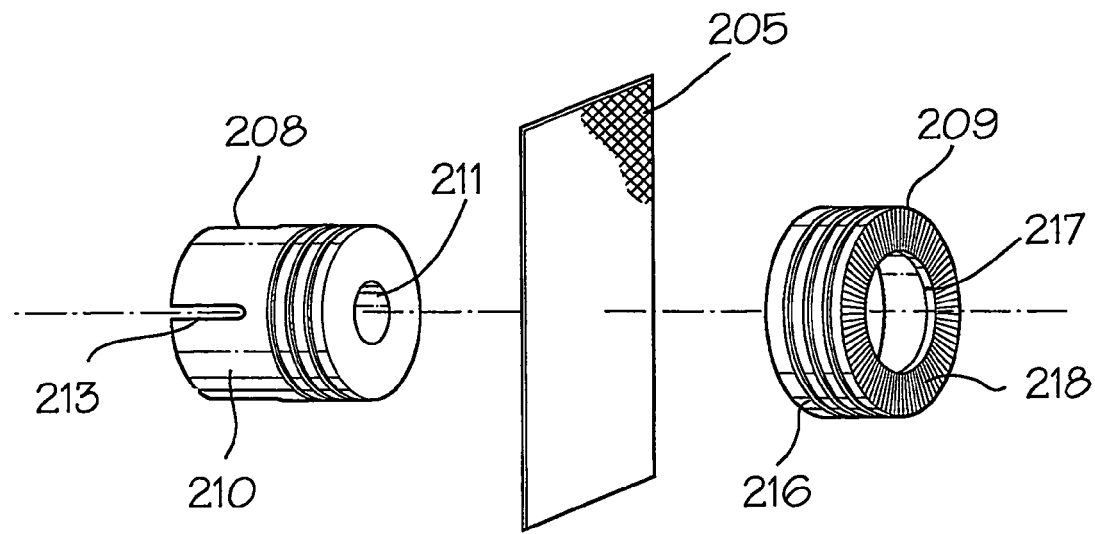
FIG. 33 is an exploded, isometric view of a sterile pad and holder for the pad.
Figure 34:
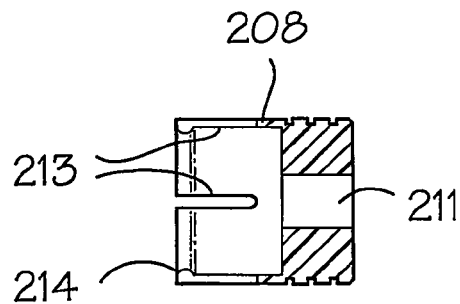
FIG. 34 is a longitudinal sectional view of a sleeve used in the holder of FIG. 33.
Figure 35:
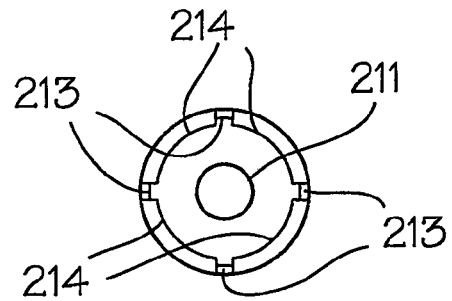
FIG. 35 is an end view of the sleeve of FIG. 34 as seen from the left thereof.
Figure 36:
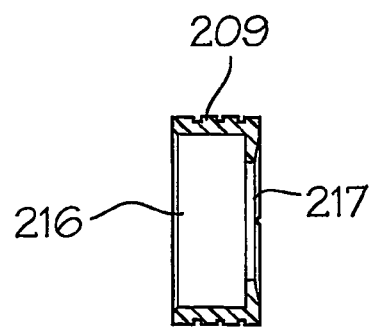
FIG. 36 is a longitudinal sectional view of a cap used in the holder of FIG. 33.

A pad 205 is held in place on the discharge end of the barrel 26 by a holder including a sleeve 208, which snaps onto the cap 91, and a cover 209 which is placed over the pad 205 and the sleeve 208. As best shown in FIGS. 33 to 35, the sleeve 208 includes a tubular body 210 with a partially closed end containing a passage 211 for receiving the nozzle of the injector. Longitudinally extending slots 213 in the rear end of the body 210 permit flexing of the body to facilitate placing of the sleeve 208 on the cap 91. An inwardly extending, annular flange 214 on the open rear end of the body 210 holds the sleeve on the cap 91. A pad 205 is placed over the end of the sleeve 208 containing the passage 211 and the cover 209 is slid onto the pad.

The cover 209 includes a tubular body 216 with an inwardly and slightly rearwardly extending annular flange 217 at the outlet end thereof. Alternating ribs and grooves or serrations 218 on the outer surface of the flange 217 grip the skin of a person receiving an injection. It will be appreciated that the sterile pad can be circular for insertion into the cover 209 to overlap the opening in the flange 217.

Alternatively, the sleeve 208 and the cover 209 can be replaced by a one-piece holder 220 (FIGS. 37 and 38) for carrying a disposable keyhole-shaped sterile pad 221 (FIG. 39) to eliminate the possibility of cross contamination. The holder 220 is defined by a tubular body 223 similar in shape to the sleeve 208. The body 223 includes longitudinally extending slots 224 permitting flexing of the body for placing the holder on a cap 91 on the discharge end of an injector. Inwardly extending, arcuate flanges 225 (one shown—FIG. 37) engage the rear end of the cap 91 to releasably retain the holder on the cap. The circular bottom end 227 of the pad 221 is inserted into the open top end of a circular slot 228 in the front end of the body 223. The top end of the pad 221 defines a tab 229, so that the pad can be handled manually without fear of contamination. Fluid is discharged through an opening 230 in the front end of the body 223. Radially extending serrations 231 on the front end grip the skin of a person receiving an injection.

Figure 37:
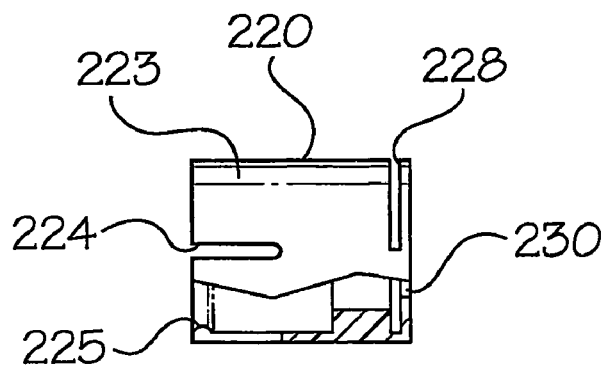
FIG. 37 is a partly sectioned side view of an alternative form of sterile pad holder.
Figure 38:
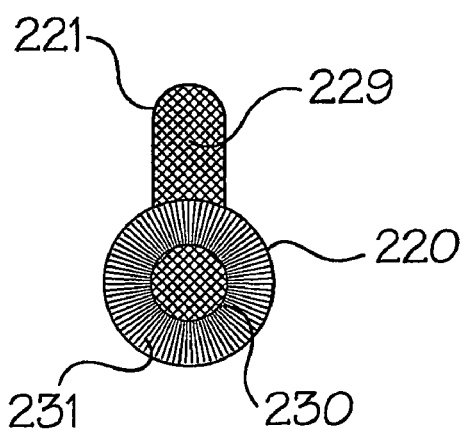
FIG. 38 is a front end view of the holder of FIG. 37 with a sterile pad therein.
Figure 39:
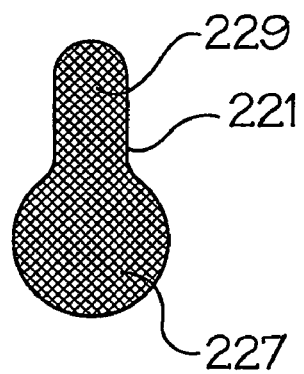
FIG. 39 is a front view of a sterile pad used in the holder of FIGS. 37 and 38.

Yet another embodiment of the sterile pad assembly includes a one-piece holder similar to that illustrated in FIGS. 37 and 38 without the slot. A sterile pad is incorporated in the holder, which is designed for single use, i.e. the holder and pad are disposable.

Figure 40:
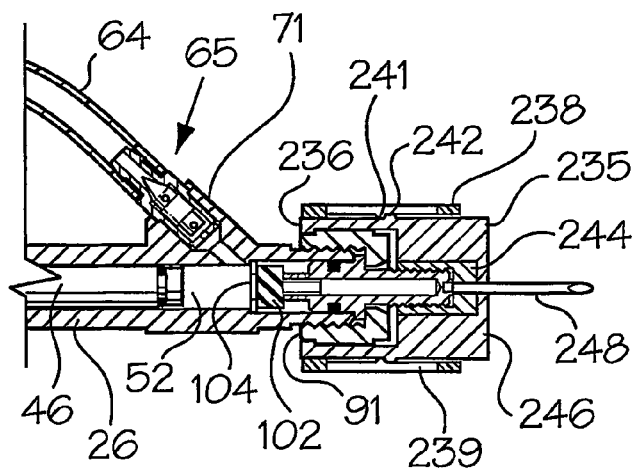
FIG. 40 is a longitudinal sectional view of the discharge end of the injector of FIG. 1 or 21 modified to accept a disposable needle.
Figure 42:
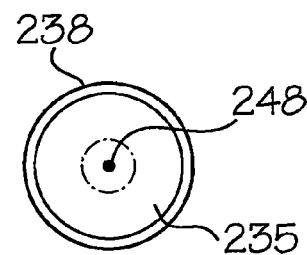
FIG. 42 is an end view of the injector of FIG. 40 as seen from the right thereof.
Figure 41:
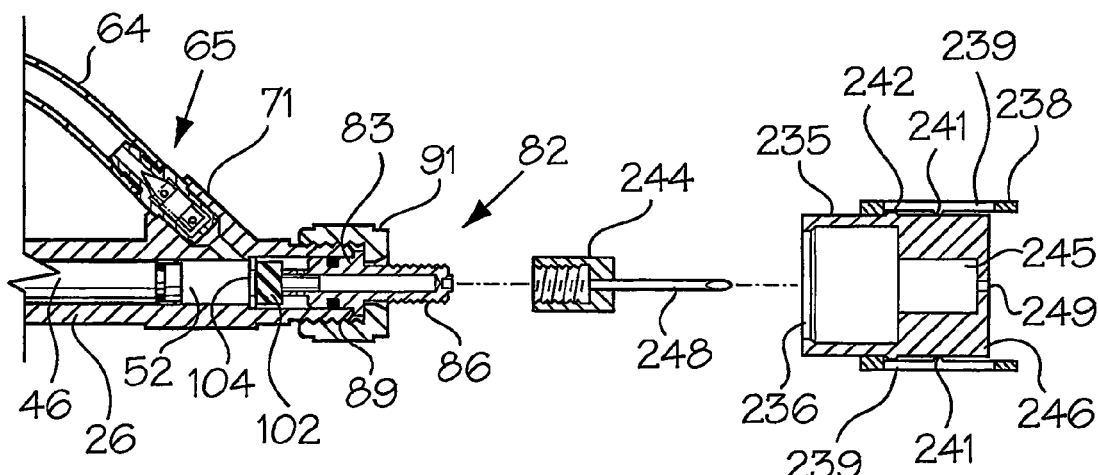
FIG. 41 is an exploded, longitudinal sectional view of the end of the injector of FIG. 40.

Referring to FIGS. 40 to 42, the injector of the present invention can readily be adapted for injections using a needle or needles. A suitable adapter for this purpose includes a tubular body 235 with an open inner end for snap fitting onto a cap 91 on the discharge end of the injector barrel 26. An annular inwardly extending flange or beaded edge 236 in the open end of the body grips the inner end of the cap 91 when the adapter is placed on the injector. A sleeve 238 is slidably mounted on the body 235 for releasably locking the latter in position on the cap 91. Longitudinally extending slots 239 in the sleeve permit flexing of the latter for movement on the body 235. Arcuate, inwardly extending, central ribs 241 in the sleeve 238 engage an annular, outwardly extending rib 242 on the body 235 for releasably locking the rear end of the sleeve on the body and the body on the cap 91.

Figure 43:
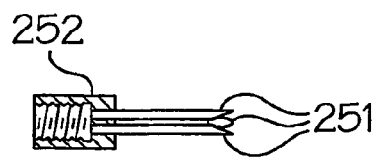
FIG. 43 is a longitudinal sectional view of a holder and multiple needles.
Figure 44:
FIG. 44 is an end view of the needles and holder of FIG. 43 as seen from the right thereof.

With the spreader 110 (FIGS. 1 and 21) removed, an internally threaded needle carrier 244 is mounted on the externally threaded outlet end 86 of the nozzle 82. The adapter is slid over the carrier 244 and onto the cap 91. The needle carrier extends into a narrow diameter passage 245 in the front or outer end 246 of the body 235, and a needle 248 in the carrier extends outwardly through a small opening 249 in the end 246 of the body. When injection using multiple needles 251 (FIGS. 43 and 44) is required, the carrier 244 is replaced with a multiple needle carrier 252 which reduces the pressure of the liquid discharged into a body.

The apparatus described above can be used to inject a liquid into humans and animals such as horses, cows, pigs and chickens at operating pressures of 55 to 250 psi, depending on the thickness and toughness of the skin.

The embodiments of the invention in which an exclusive property or privilege is claimed are defined as follows:

1. A needleless injector comprising:
    a barrel for receiving an injectable liquid from a source thereof;
    a nozzle in one end of said barrel for discharging liquid from said barrel;
    a plunger slidable in said barrel for movement between a retracted position in which liquid is drawn into said barrel between said nozzle and said plunger and an extended position in which liquid is discharged through said nozzle;
    a piston slidable in said barrel for retaining said plunger in the retracted position and movable under fluid pressure to move said plunger to the extended position;
    a retractor in said barrel for moving said plunger to the retracted position when said piston is retracted;
    a coupler connecting said retractor to said plunger permitting sliding of said piston in said barrel against said plunger to move the latter to the extended position, and for drawing the plunger to the retracted position when the piston and retractor are moved in a direction away from said nozzle to the retracted position;
    a first valve for introducing fluid under pressure into said barrel alternately on one side of said piston to move the piston and plunger from the retracted to the extended position to discharge liquid through said nozzle, and on a second side of said piston to return the piston and plunger to a retracted position in which injectable liquid is drawn into the barrel between said nozzle and said plunger;
    a trigger for operating said first valve to cause said plunger to move from the retracted to the extended position and then back to the retracted position each time the trigger is operated;
    a stop in a second end of said barrel remote from said one end for limiting movement of the piston when the plunger anti piston move to the retracted position; and
    a magnet in said piston releasably retaining the piston and plunger in the retracted position until the trigger is operated.

2. The needleless injector of claim 1, including a stroke adjuster for altering the stroke of said piston and consequently the dosage of liquid discharged from said barrel.

3. The needleless injector of claim 2, wherein said stroke adjuster includes a threaded rod in said second end of said barrel for engaging said piston, whereby rotation of said rod in said barrel changes the length of the stroke of said piston.

4. The needleless injector of claim 3, wherein said stroke adjuster includes a slide in said barrel between said rod and said piston; and
    a bearing rotatably connecting said rod to said slide, whereby rotation of said rod causes a corresponding sliding of said slide in said barrel.

5. The needleless injector of claim 4, wherein said stroke adjuster includes a knob rotatably mounted on said second end of said barrel and connected to said rod for rotating said rod; and a scale on said barrel exposed by movement of said knob to indicate a dosage selling of the injector.

6. The needleless injector of claim 1, including a removable cap on said one end of said barrel for retaining said nozzle in said barrel; and a needle for removable mounting on said nozzle.

7. The needleless injector of claim 6, including an adapter for mounting on said cap for retaining said needle on said nozzle.

8. The needleless injector of claim 6, including a plurality of parallel, spaced apart needles for simultaneous injection of liquid discharged from said nozzle.

9. The needleless injector of claim 1, including a syringe on said barrel for carrying a supply of injectable liquid, and a scale on said syringe indicative of the dosage of liquid injected each time an injection is made using the injector.

10. The needleless injector of claim 9, including a one-way valve connecting said syringe to the barrel for admitting injectable liquid into said barrel when the plunger is retracted.

11. The needleless injector of claim 1, including flexible bag means in fluid communication with said barrel for carrying a supply of injectable liquid.

12. The needleless injector of claim 1, wherein said nozzle includes a plurality of orifices for discharging liquid from said barrel.

* * * * *